(12) United States Patent
Griffin et al.

(10) Patent No.: US 7,774,050 B2
(45) Date of Patent: *Aug. 10, 2010

(54) METHOD AND APPARATUS FOR THE EARLY DIAGNOSIS OF SUBACUTE, POTENTIALLY CATASTROPHIC ILLNESS

(75) Inventors: M. Pamela Griffin, Charlottesville, VA (US); J. Randall Moorman, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 860 days.

This patent is subject to a terminal disclaimer.

(21) Appl. No.: 11/000,630

(22) Filed: Dec. 1, 2004

(65) Prior Publication Data

US 2005/0137484 A1 Jun. 23, 2005

Related U.S. Application Data

(60) Division of application No. 09/770,653, filed on Jan. 29, 2001, now Pat. No. 6,856,831, which is a continuation of application No. 09/271,279, filed on Mar. 17, 1999, now Pat. No. 6,216,032.

(60) Provisional application No. 60/078,319, filed on Mar. 17, 1998.

(51) Int. Cl.
*A61B 5/0402* (2006.01)
*A61B 5/0456* (2006.01)
*A61B 5/0444* (2006.01)

(52) U.S. Cl. .................. 600/511; 600/508; 600/513; 600/521

(58) Field of Classification Search ............. 600/511, 600/508–509, 513, 521
See application file for complete search history.

(56) References Cited

U.S. PATENT DOCUMENTS

| | | | | | |
|---|---|---|---|---|---|
| 3,888,240 | A | * | 6/1975 | Reinhold et al. | 600/390 |
| 3,989,034 | A | * | 11/1976 | Hojaiban | 600/511 |
| 5,042,499 | A | * | 8/1991 | Frank et al. | 600/511 |
| 5,718,235 | A | * | 2/1998 | Golosarsky et al. | 600/515 |
| 5,755,671 | A | * | 5/1998 | Albrecht et al. | 600/516 |
| 5,954,663 | A | * | 9/1999 | Gat | 600/511 |
| 5,957,855 | A | * | 9/1999 | Oriol et al. | 600/511 |
| 5,995,868 | A | * | 11/1999 | Dorfmeister et al. | 600/544 |
| 6,216,032 | B1 | * | 4/2001 | Griffin et al. | 600/515 |
| 6,330,469 | B1 | * | 12/2001 | Griffin et al. | 600/515 |

* cited by examiner

*Primary Examiner*—Carl H Layno
*Assistant Examiner*—Natasha N Patel
(74) *Attorney, Agent, or Firm*—Novak Druce DeLuca + Quigg LLP; Robert J. Decker (57) ABSTRACT

In one aspect of the invention, there is provided a method and apparatus for early detection of subacute, potentially catastrophic infectious illness in a premature newborn infant. The method comprises: (a) continuously monitoring heart rate variability in the premature newborn infant; and (b) identifying at least one characteristic abnormality in the heart rate variability that is associated with the illness. This method can be use to diagnose illnesses such as, but not limited to, sepsis, necrotizing enterocolitis, pneumonia and meningitis. In another aspect of the present invention, there is provided a method and apparatus for early detection of subacute, potentially catastrophic infectious illness in a patient. The method comprises: (a) continuously monitoring the patient's RR intervals; (b) generating a normalized data set of the RR intervals; (c) calculating one or more of (i) moments of the data set selected from the third and higher moments and (ii) percentile values of the data set; and (d) identifying an abnormal heart rate variability associated with the illness based on one or more of the moments and the percentile values.

9 Claims, 6 Drawing Sheets

METHOD AND APPARATUS FOR THE EARLY DIAGNOSIS OF SUBACUTE, POTENTIALLY CATASTROPHIC ILLNESS

This application is a divisional application of U.S. application Ser. No. 09,770, 653, filed Jan. 29, 2001 now U.S. Pat. No. 6,856,831, which is a continuation application of application Ser. No. 09/271,279, filed Mar. 17, 1999, now U.S. Pat. No. 6,216,032 B1, which claims benefit under 35 U.S.C. Section 119(e) from U.S. Provisional Application No. 60/078,319 filed on Mar. 17, 1998 and U.S application Ser. No. 09/770,653 filed on Dec. 1, 2004 and entitled "Device to Make the Early Diagnosis of Subacute, Potentially Catastrophic Illness", now U.S. Pat. No. 6,856,831, the disclosures of which are hereby incorporated by reference herein in their entirety.

This application is related to U.S. application Ser. No. 09/668,309, filed Sep. 25, 2000, now U.S. Pat. No. 6,330,469 B 1, entitled "Method and Apparatus for the Early Diagnosis of Subacute, Potentially Catastrophic Illness" and U.S. application Ser. No. 09/793,653, filed Feb. 27, 2001, now U.S. Pat. No. 6,804,551 B2, entitled "Method and Apparatus for the Early Diagnosis of Subacute, Potentially Catastrophic Illness," the disclosures of which are hereby incorporated by reference herein in their entirety.

FIELD OF THE INVENTION

The present invention relates to the indication of early phases of potentially catastrophic illnesses and relates to heart rate variability monitoring in patients.

BACKGROUND OF THE INVENTION

Approximately 40,000 very low birth weight ("VLBW") infants (less than 1,500 gm) are born in the United States each year. Ventura et al., "Advance report of final natality statistics, 1994." *Monthly Vital Statistics Report* 1996; 44:1-88. Survival of this group has improved with advances in neonatal intensive care, but late-onset sepsis and necrotizing enterocolitis ("NEC") continue to be major causes of morbidity and mortality. Stoll B J, Gordon T, Korones S B, Shankaran S, Tyson J E, Bauer C R, "Late-onset sepsis in very low birth weight neonates: a report from the National Institute of Child Health and Human Development Neonatal Research Network." *Journal of Pediatrics* 1996; 129:63-71. Gray J E, Richardson D K, McCormick M C, Goldmann D A, "Coagulase-negative staphylococcal bacteremia among very low birth weight infants: relation to admission illness severity, resource use, and outcome." *Pediatrics* 1995; 95:225-230. Unfortunately these illnesses are common in neonates, and infected infants have a significant increase in the number of days spent on the ventilator and an average increase in duration of hospital stay of 25 days. See Stoll et al. above.

Neonatal sepsis occurs in 5 to 15% of infants weighing less than 1,500 gm at birth, and the rate is about 1 per 100 patient days. Gladstone, I. M., R. A. Ehrenkrantz, S. C. Edberg, and R. S. Baltimore. 1990. "A ten-year review of neonatal sepsis and comparison with the previous fifty year experience." *Pediatric Infectious Disease Journal* 9:819-825. Moro, M. L., A. DeToni, I. Stolfi, M. P. Carrieri, M. Braga, and C. Zunin. 1996. "Risk factors for nosocomial sepsis in newborn infants and intermediate care units." *European Journal of Pediatrics* 155:315-322. The National Institute of Child Health & Human Development ("NICHED") Neonatal Research Network found that neonates who develop late-onset sepsis have a 17% mortality rate, more than twice the 7% mortality rate of noninfected infants.

Risk factors for late-onset sepsis are ubiquitous in the NICU: intubation, umbilical catheters, prolonged mechanical ventilation, low birth weight, parenteral nutrition via central venous catheters, respiratory distress syndrome, bronchopulmonary dysplasia, severe intraventricular hemorrhage, and nasogastric and tracheal cannulae are all independently associated with sepsis. See Moro et al. supra. Each interventional device represents a potential source of infection and increases the risk of catastrophic infectious illness. Id.

Necrotizing enterocolitis affects up to 4,000 infants in the U.S. yearly, and an estimated 10 to 50% of infants who develop NEC die. Neu, J. 1996. "Necrotizing enterocolitis." *Pediatric Clinics of North America* 43:409-432. Infants who develop NEC often require intubation and an increase in respiratory support. Survivors are often left with strictures and short-bowel syndrome.

Unfortunately, prior to the discovery of the present invention there has been no reliable clinical means for early diagnosis of these diseases. Clinical neonatologists caring for these VLBW infants recognize sepsis and NEC as potentially catastrophic illnesses, and thus do not hesitate to obtain blood cultures and to administer antibiotics empirically at the first appearance of symptoms in an attempt to avert disaster. Likewise, physicians do not hesitate to stop feeding and obtain radiographic studies should any abdominal finding occur. Unfortunately, clinical signs are neither sensitive nor specific in these illnesses, resulting in many unnecessary blood cultures, unnecessary administration of short courses of antibiotics given to infants without bacterial infection, and unnecessary interruptions in neonatal nutrition. Moreover, despite these practices, sepsis and necrotizing enterocolitis continue to occur and continue to cause neonatal deaths. Indeed, by the time clinical signs and symptoms for either sepsis or NEC have developed, the illness may have progressed to an irreversible stage. Thus a successful surveillance strategy which leads to an earlier diagnosis of sepsis and NEC for the VLBW infants is necessary and critical in decreasing mortality and morbidity.

In healthy newborn infants, time series of heart period (or RR intervals, the time between successive heart beats) show obvious variability. Numerous publications are available which detail the measurement and characterization of such heart rate variability (HRV). See, e.g., 1. Ori, Z., G. Monir, J. Weiss, X. Sayhouni, and D. H. Singer. 1992. "Heart rate variability: frequency domain analysis." *Cardiology Clinics* 10:499-533. Kleiger, R. E., P. K. Stein, M. S. Bosner, and J. N. Rottman. 1992. "Time domain measurements of heart rate variability." *Cardiology Clinics* 10:487-498. HRV arises from the interplay of the sympathetic and parasympathetic arms of the autonomic nervous system, which act respectively to speed or slow the heart rate. In newborn infants, as in adults, HRV is substantially reduced during severe illness. Burnard, E. D. 1959. "Changes in heart size in the dyspnoeic newborn infant." *Brit Med J* 1:1495-1500. Rudolph, A. J., C. Vallbona, and M. M. Desmond. 1965. "Cardiodynamic studies in the newborn. III. Heart rate patterns in infants with idiopathic respiratory distress syndrome." *Pediatrics* 36:551-559. Cabal, L. A., B. Siassi, B. Zanini, J. E. Hodgman, and E. E. Hon. 1980. "Factors affecting heart rate variability in preterm infants." *Pediatrics* 65:50-56. Griffin, M. P., D. F. Scollan, and J. R. Moorman. 1994. "The dynamic range of neonatal heart rate variability." *J. Cardiovasc. Electrophysiol.* 5:112-124.

The reasons for reduced HRV during illness has been debated, and three theories concerning the mechanisms of reduced HRV have been developed. These theories focus on the mathematical characteristics of RR interval time series showing normal and low HRV.

The first theory focuses on the notion that the mechanism behind reduced HRV is a reduction of parasympathetic tone. Akselrod, S., D. Gordon, F. A. Ubel, D. C. Shannon, A. C. Barger, and R. J. Cohen. 1981. "Power spectrum analysis of heart rate fluctuation: a quantitative probe of beat-to-beat cardiovascular control." *Science* 213:220-222. But see Malik, M. and A. J. Camm. 1993. "Heart rate variability: from facts to fancies." *J Am Coll Cardiol* 22:566-568. The second theory centers on the notion that normal physiology is more complex than abnormal, hence heart rhythm is more irregular during health. Goldberger, A. L., D. R. Rigney, and B. J. West. 1990. "Chaos and fractals in human physiology." *Scientific American* 262:42-46. Goldberger, A. L., V. Bhargava, B. J. West, and A. J. Mandell. 1985. "On a mechanism of cardiac electrical stability: the fractal hypothesis." *Biophys J* 48:525-528. Goldberger, A. L. and B. J. West. 1987. "Chaos in physiology: health or disease? In Chaos in biological systems." H. Degn, A. V. Holden, and L. F. Olsen, editors. Plenum Press, New York. 1-4. Goldberger, A. L. and B. J. West. 1987. "Applications of nonlinear dynamics to clinical cardiology." *Ann NY Acad Sci* 504:195-213. Goldberger, A. 1990. "Fractal electrodynamics of the heartbeat. In Mathematical Approaches to Cardiac Arrhythmias." J. Jalife, editor. The New York Academy of Sciences, New York. 402-409. Peng, C.-K., J. Mietus, J. M. Hausdorff, S. Havlin, H. E. Stanley, and A. L. Goldberger. 1993. "Long-range anticorrelations and non-Gaussian behavior of the heartbeat." *Phys Rev Lett* 70:1343-1346.

Without wishing to be held to any particular explanation or theory, we have developed a third theory of the mechanism of the observed abnormalities of HRV: an explanation based on the events of signal transduction cascades (Nelson J C, Rizwan-uddin, Griffin M P, Moorman J R. Probing the order of neonatal heart rate variability. *Pediatric Research,* 43: 823-831, 1998). The sinus node cell membrane has beta-adrenergic receptors which, on binding agonists released from sympathetic nerve endings or the adrenal medulla, lead to the activation of cAMP-dependent protein kinase, which phosphorylates cardiac ion channels and results in cell depolarization, an action potential, and a heartbeat. This readily explains the rise in heart rate after sympathetic stimulation. The sinus node cell membrane also contains muscarinic acetylcholine receptors—when bound with acetylcholine from parasympathetic nerve endings, the process is inhibited and the heart rate falls. As the amounts of sympathetic and parasympathetic activity vary, so heart rate varies. Thus, for as long as the complex steps of intracellular signal transduction can be successfully completed, we can view the sinus node as an amplifier of the input signals of the autonomic nervous system, and heart rate as the output signal.

Consider now a severe illness such as sepsis. In such an unfavorable metabolic milieu, optimal conditions for signal transduction are unlikely. We hypothesize that HRV becomes abnormal here because sinus node cells, like all other cells, are unable to respond normally to sympathetic and parasympathetic inputs. From this viewpoint, sinus node cells report in real time on their ability to respond to adrenergic and muscarinic stimuli. Effective reporting depends on optimal intracellular conditions, and we view HRV as a sensitive measure of the state of cells.

We thus hypothesized that monitoring HRV in patient populations at high risk leads to an early diagnosis and opportunity for early treatment for severe infections. We have found this to be the case. In particular, we have found that records of RR intervals in infants prior to the clinical diagnosis of sepsis demonstrate at least two characteristic abnormalities. First, the baseline shows very reduced variability. Second, there are short-lived episodes of deceleration of heart rate. We have developed novel mathematical approaches to detecting these characteristic abnormalities.

Heretofore, heart rate variability measurement has been used as a means of assigning long-term prognosis, usually in adults with heart disease. These measurements, however, typically involve only a single measurement of HRV rather than the continuous monitoring we describe.

Heart rate variability (HRV) is abnormal during neonatal illness, but the value of monitoring HRV as a means of early diagnosis of sepsis and necrotizing enterocolitis in premature neonates has not heretofore been tested. Conventional measures of HRV fail to detect the abnormal HRV in the infants because these measurements, such as standard deviation and power are optimized to detect low variability. Additionally, prior studies showing low HRV in newborn infants with severe illness have typically focused on term rather than premature infants. See, e.g., Griffin M P, Scollan D F, Moorman J R. "The dynamic range of neonatal heart rate variability." *Journal of Cardiovascular Electrophysiology* 1994; 5:112-124.

BRIEF DESCRIPTION OF THE DRAWINGS

FIGS. 1E-H show the corresponding frequency histograms of RR intervals. All were recorded from the same infant who developed coagulase-negative staphylococcal septicemia and an enterococcal urinary tract infection.

SUMMARY OF THE INVENTION

In one aspect of the invention, there is provided a method for early detection of subacute, potentially catastrophic infectious illness in a premature newborn infant. The method comprises: (a) continuously monitoring heart rate variability in the premature newborn infant; and (b) identifying at least one characteristic abnormality in the heart rate variability that is associated with the illness.

This method can be use to diagnose illnesses such as, but not limited to, sepsis, necrotizing enterocolitis, pneumonia and meningitis.

Preferably, a one or more diagnostic work-ups are conducted for a suspected illness when the at least one characteristic abnormality is identified. Such diagnostic work-ups include, but are not limited to, obtaining blood cultures, taking X-rays, or obtaining pathological specimens from the newborn infant.

In one preferred embodiment, the at least one characteristic abnormality is identified from a normalized data set of RR intervals. A substantially large data set is preferred. Such a data set more preferably contains on the order of about $10^3$ to $10^4$ RR intervals.

The at least one characteristic abnormality is preferably identified based on at least one of the third and higher moments (more preferably the third and fourth moments), percentile values (more preferably the 10th percentile value), variance, standard deviation and coefficient of variation of the normalized data set.

In another aspect of the present invention, there is provided a method for early detection of subacute, potentially catastrophic infectious illness in a patient. The method comprises: (a) continuously monitoring the patient's RR intervals; (b) generating a normalized data set of the RR intervals; (c) calculating one or more of (i) moments of the data set selected from the third and higher moments and (ii) percentile values of the data set; and (d) identifying an abnormal heart rate variability associated with the illness based on one or more of the moments and the percentile values.

Figure 6:
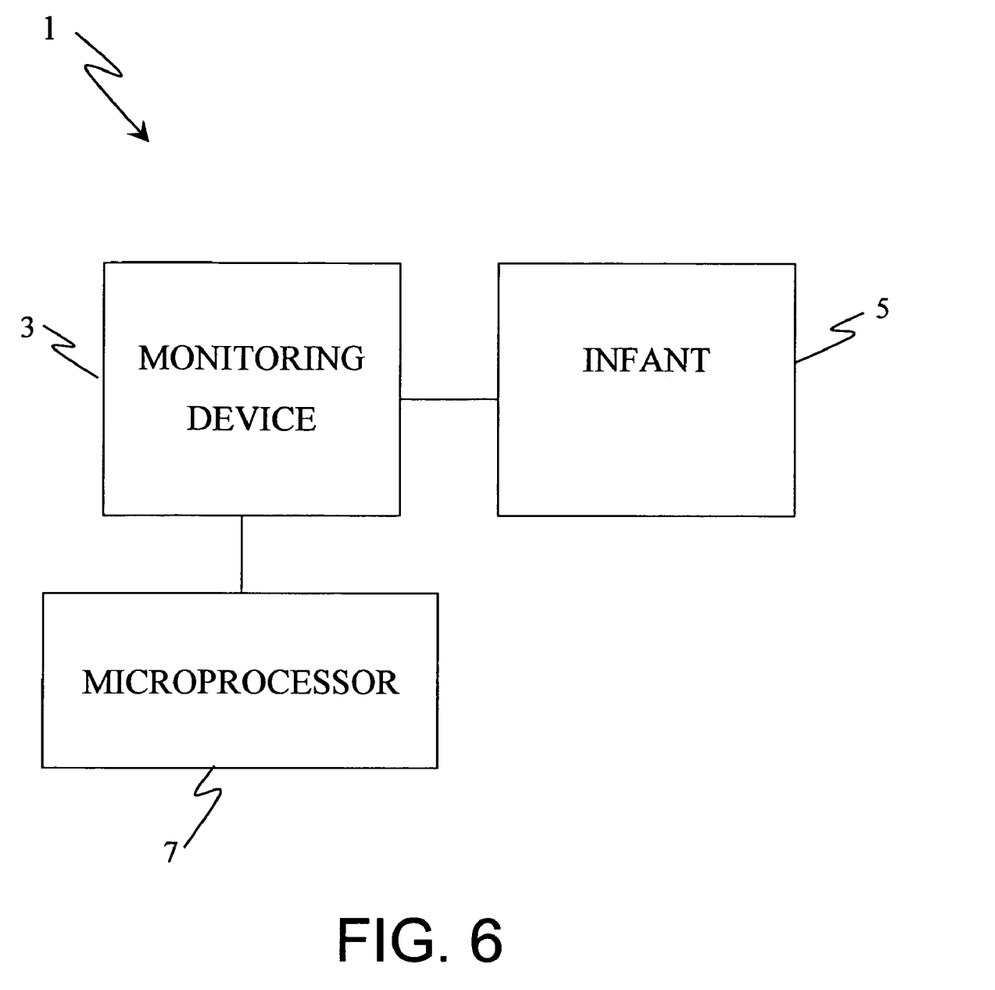
FIG. 6 illustrates the apparatus comprising the monitoring device and the microprocessor in relation to the infant.

In yet another aspect of the present invention, there is provided an apparatus for early detection of subacute, potentially catastrophic infectious illness in a premature newborn infant. The apparatus 1 comprises: (a) a monitoring device 3, continuously monitoring heart rate variability in the premature newborn infant 5; and (b) a microprocessor 7, identifying at least one characteristic abnormality in the heart rate variability that is associated with the illness. The microprocessor preferably generates a normalized data set of RR intervals and also preferably calculates one or more of the third and higher moments of the data set (more preferably skewness and/or kurtosis) and the percentile values of the data set (more preferably 10th percentile) and identifies the characteristic abnormality based on the same.

Still another aspect of the present invention concerns an apparatus for early detection of subacute, potentially catastrophic infectious illness in a patient. The apparatus 1 comprises (1) a monitoring device 3, continuously monitoring the patient's RR intervals 5, and (2) a microprocessor 7. The microprocessor 7 performs steps comprising: (a) generating a normalized data set of the RR intervals; (b) calculating one or more of (i) moments of the data set selected from the third and higher moments and (ii) percentile values of the data set; (c) identifying an abnormal heart rate variability based on one or more of the moments and the percentile values.

DETAILED DESCRIPTION OF THE INVENTION

The present invention relates to successful neonatal HRV monitoring, and the ability to distinguish abnormal HRV from normal HRV using objective criteria. Neonatal HRV correlates with the severity of neonatal illness such that a decrease in HRV occurs before clinical manifestations of sepsis and necrotizing enterocolitis appear.

The invention relates to a real-time heart rate variability monitor whose signal can be interpreted as the probability of an impending catastrophic clinical event. The present invention can be applied in patient populations that are at high risk of potentially catastrophic impending events such as, but not limited to, sepsis, necrotizing enterocolitis, pneumonia and meningitis.

The invention relates to a process by which continuous monitoring of novel parameters of heart rate variability can be used to make the early diagnosis of subacute illness in premature newborns.

The analysis of the present invention preferably includes the following steps to construct a digitally filtered and normalized data set from data sets of sufficient numbers of consecutive RR intervals:

1. Acquire continuous EKG signal and RR interval time series data.
2. Separate into piecewise continuous beat records (e.g., the 4096 beat records used in the Examples).
3. Filter, for example, using a (2M+1) point moving average filter.

$$RR_{(n)} = \frac{1}{2M+1} \sum_{j=-M}^{M} RR_{(n-j)}$$

4. Calculate the mean, variance and standard deviation of each record.
5. Normalize the data by subtracting the mean and dividing by the standard deviation.
6. Calculate, for example, the third and fourth moments of the normalized data, where:

$$m_r = \frac{1}{N} \sum_{j=1}^{N} (X_j - X_{ave})^r$$

where $m_r$ is the rth moment of the time series variable X. The moment coefficient of skewness is $m_3/(m_2)^{3/2}$, and the moment coefficient of kurtosis is $m_4/(m_2)^2$. When the data are normalized, $m_2$ (the variance) is 1, and the third and fourth moments are identical to the skewness and the kurtosis, respectively.

7. Determine percentiles of the normalized filtered data by sorting the intervals from smallest to largest. The 50th percentile value, or P50, is the value halfway from smallest to largest. It is the median value of the data set. In the same way, other percentile values of interest can be determined. For example, P10 is the value that lies 10% of the way between the smallest and the largest. For our data sets of 4096 points, it is the 410th point starting from the smallest.

The present invention also relates to novel parameters of heart rate variability which include, but are not limited to, the following:

1. Higher moments of the data, including
   a. The third moment of the digitally filtered and normalized data set (the moment coefficient of skewness, also referred to simply as "skewness"): a high positive value indicates the presence of short-lived subclinical decelerations in heart rate, which allows for a diagnosis early in the course of subacute illnesses, such as sepsis.
   b. The fourth moment of the filtered and normalized data set (the moment coefficient of kurtosis, also referred to simply as "kurtosis"): a high positive value indicates a peaked frequency histogram of the RR intervals, which allows for a diagnosis early in the course of subacute illnesses, such as sepsis.
2. Percentiles of the data, such as the 10th percentile value of the filtered and normalized data set (P10): a value closer to 0 allows for a diagnosis early in the course of subacute illnesses, such as sepsis. Other reasonably low percentiles (e.g., P1 to P20) are likely to be equally appropriate. Moreover, characteristic abnormalities of other percentile values (for example, the 25th, 50th (median), 75th and 90th percentile values of data set) are contemplated.

Graphically, the third and fourth moments report on the nature of the frequency histogram of the RR intervals. Specifically, the third moment reports on the symmetry of the histogram, and becomes large as the histogram is skewed to the right by the long RR intervals associated with the episode of relative bradycardia. Since the variance of the normalized record is 1, the third moment is referred to as the skewness. The fourth moment reports on the nature of the peak, and becomes larger as the peak becomes sharper. Since records with predominantly low HRV have RR interval values that are tightly clustered, the histogram has a sharp main peak, and the fourth moment is relatively large. Since the variance of the normalized record is 1, the fourth moment is referred to as the kurtosis. Thus one aspect of the present invention relates to the examination of records for elevated values of skewness and kurtosis.

Abnormalities in HRV that are characteristic of illness can be identified, for example, by comparing the above parameters of heart rate variability to threshold or by combining multiple measurements of HRV using logistic regression models, neural networks or other predictive mathematical instruments. Appropriate parameters for thresholds or for mathematical modeling can be assigned by those skilled in the art. Ideally, these parameters will be based on the results of a large group, for example, a group of newborn infants at risk of sepsis and necrotizing enterocolitis. For example, from the infants observed to date, reasonable threshold values include: skewness on the order of about 1 or more, kurtosis on the order of about 7 or more and P 10 on the order of about −1.1 or more.

EXAMPLES

Example 1

Neonatal infants in the NICU who were at risk for developing late-onset sepsis or necrotizing enterocolitis were studied. Infants were selected for monitoring if they were low birth weight, premature, likely to need central venous access, and likely to remain in the NICU for longer than two weeks. The infants were assigned to 1 of 2 groups as follows: "control" infants had no clinical suspicion of illness or cultures obtained; "event" infants had a positive blood culture with clinical illness or necrotizing enterocolitis. Late-onset sepsis was defined as one or more positive blood cultures obtained after 72 hours of age with clinical signs and symptoms suggestive of infection including apnea and bradycardia, the need for increased respiratory support, or feeding intolerance. Blood cultures were obtained at the discretion of the infants' physicians. The timing and results of blood cultures were obtained from the microbiology report and confirmed with the bedside record. NEC was diagnosed in infants who were clinically ill and who had pneumatosis intestinalis on a radiograph. Time-domain and frequency-domain parameters of heart rate variability were measured for up to 7 days before and 3 days after events or a random "pseudoevent." There were 30 events in 27 patients (26 positive blood cultures and 4 episodes of necrotizing enterocolitis). In the control group 31 pseudoevents were assigned to 28 patients. In the infants who had an event, abnormal HRV were observed preceding the event characterized by reduced baseline variability and subclinical, short-lived decelerations in heart rate. While conventional time- and frequency-domain measures did not change, two novel measures of the present invention—skewness and the 10th percentile value—changed significantly 12 to 24 hours before the event.

Commercially available digital signal processing and analog-digital conversion boards (National Instruments AT-DSP2200) in a 80486-based microcomputer were used for processing and calculating data. Each PC allows monitoring of two infants. The application was written in C++. A reconstituted analog EKG voltage signal from the sync/defib outlet of the bedside monitor (Marquette), which is standard of care in the NICU, was digitized and digitally high-pass filtered, and then evaluated for peaks corresponding to QRS complexes using amplitude and duration criteria, which are established automatically. During development of the system, the QRS identification scheme was verified to be accurate using recorded EKG signals of multiple configurations. Aberrant and artifactual RR intervals were identified using schemes based on the previous RR interval history. The proportion of acceptable intervals was continuously monitored. When it fell below a threshold value, the digitized EKG signal was again evaluated and new threshold and duration criteria were established. From the lists of RR intervals, HRV measures were calculated. FORTRAN programs were used offline to calculate moments and percentiles of the data. Piecewise continuous 4096 beat records were de-trended using a ten-point moving average filter. Calculations were repeated every 32 beats, about every 5 seconds.

The mean and variance (first and second moments) of each filtered record were calculated and used to normalize the data so that the mean and variance of each record were 0 and 1 respectively. The third (skewness) and fourth (kurtosis) moments of the filtered, normalized data were calculated. Approximate entropy, a measure of regularity (see Pincus S M. "Approximate entropy as a measure of system complexity." Proc. Natl. Acad. Sci. 1991; 88:2297-2301) was also determined, along with the 10th, 25th, 50th, 75th, and 90th percentile data points.

A strategy for interpolation of a continuous heart rate signal described by Berger and co-workers was used. Berger R D, Akselrod S, Gordon D, Cohen R J. "An efficient algorithm for spectral analysis of heart rate variability." *IEEE Trans. Biomed. Eng.* 1986; BME-33:900-904. Power spectra of overlapping 1024 beat segments were calculated after applying a split cosine bell window and then averaged. Quadrature was used to calculate the power in bandwidths 0 to 0.02, 0 to 0.04, 0.02 to 0.2, 0.04 to 0.2, and 0.2 to 0.5 Hz. See Van Ravenswaaij-Arts C, Hopman J, Kollee L, Stoelinga G, VanGeijn H. "Spectral analysis of heart rate variability in spontaneously breathing very preterm infants." *Acta Paediatrica Scandinavica* 1994; 83:473-480. Chatow U, Davidson S, Reichman B L, Akselrod S. "Development and maturation of the autonomic nervous system in premature and full-term infants using spectral analysis of heart rate fluctuations." *Pediatr. Res.* 1995; 37:294-302.

As a reference point was used the time that the blood culture was drawn or the time of radiographic evidence of pneumatosis intestinalis (events group) or a random time (controls group) based on availability of data. Data in 12-hour epochs for up to 7 days before and up to 3 days afterwards was analyzed. Moments, percentiles, frequency in several bands, and approximate entropy for all the 4096 beat data sets were calculated, and summarized each 12-hour epoch as the median value of each measure for each patient. The heart rate database for each 12-hour epoch for each patient consisted of 15 measures: the medians of four moments, approximate entropy, five percentiles, and five frequency bands.

Sets of heart rate measures often failed a test for normality, and the significance of differences between groups was examined using the Mann-Whitney rank sum test (SigmaStat, Jandel).

Table 1 shows the demographic characteristics of the infants studied:

TABLE 1

Population Characteristics.

| | Controls (n = 28) | Events (n = 27) |
|---|---|---|
| Birth weight, g | | |
| <750 | 4 | 12 |
| 750-999 | 13 | 8 |
| 1000-1499 | 10 | 5 |
| >1500 | 1 | 2 |
| Gestation age, wk | | |
| <26 | 6 | 11 |
| 26-28 | 10 | 9 |
| 29-32 | 10 | 6 |
| >32 | 2 | 1 |
| Post-conceptional age at event, wk | | |
| 26-28 | 0 | 6 |
| 29-32 | 11 | 14 |
| >32 | 20 | 10 |
| Male sex | 15 | 14 |
| Caucasian | 23 | 20 |

As previously noted, there were 30 events in 27 patients (26 positive blood cultures and 4 cases of NEC). There were 2 deaths, associated with *Staphylococcus aureus* and enterococcal septicemia. The most common organisms isolated were coagulase-negative *Staphylococcus* (n=10) and *Staphylococcus aureus* (n=9). In the control group, there were 31 randomly assigned "pseudoevents" in 28 patients. In the events group, the mean (SD) birth weight, gestational age and post-conceptional age at event were 904 g (483), 26.6 weeks (3.1), and 31.5 weeks (3.6), respectively. In the control infants, the values were 968 g (264), 28.2 weeks (2.7), and 33.1 weeks (2.5), respectively. Infants in the events group had lower gestational ages (p=0.046. t-test) and a trend toward lower post-conceptional ages (p=0.060). The difference in birth weights was not statistically significant (p=0.543).

Panel A of FIG. 1 shows a time series of 4096 RR intervals from an infant 10 days prior to an episode of sepsis and represents normal HRV. Panels B to D show abnormal RR interval time series from the same infant obtained 1 to 3 hours before sepsis was suspected and blood cultures were obtained. (The infant developed coagulase-negative staphylococcal septicemia and an enterococcal urinary tract infection.) The variance, skewness and 10th percentile of the data sets are:

(A) 278, 0.3, −1.23; (B) 11, 1.8, −1.10; (C) 57, 3.4, −0.74; (D) 205, 2.6, −0.89.

Panel B shows very reduced variability. Panels C and D also have a baseline of reduced variability but are punctuated by sharp "spikes" representing short-lived episodes of heart rate decelerations (bradycardia). While episodes of bradycardia in NICU patients are common and not necessarily significant, frequent episodes are often reflect early stages of sepsis. The heart rate in these records always exceeded 120 beats per minute, and these episodes would have failed to trigger heart rate alarms set at typical thresholds of 100 beats per minute. Distinguishing panel B from normal is straightforward and may be accomplished by calculating the variance alone—11 msec$^2$ compared with 278 msec$^2$ for the normal. Variance (and the related measures standard deviation and coefficient of variation) have all been successful in detecting abnormal HRV in many clinical studies, but would fail to diagnose the abnormal time series in Panels C and D. In panel D, the episodes of sub-clinical heart rate decelerations are sufficient to elevate the variance to apparently normal values of more than 200 msec$^2$. To diagnose these abnormalities, an approach based on the frequency histograms of the RR intervals shown to the right of the time series was developed. The long RR intervals during the decelerations generated asymmetry of the histogram, with a tail to the right (G and H). The third moment or skewness reports on the symmetry of the histogram, and becomes positive and large as the histogram is skewed to the right by the long RR intervals of heart rate deceleration episode. It is calculated as the third moment of data sets with mean 0 and standard deviation 1. The abnormalities of the histograms can also be quantified by considering the relationship of values in the distribution to the mean. Accordingly, we determined the values of five percentile values—10th, 25th, 50th (the median), 75th, and 90th. We found that the largest difference occurred in the 10th percentile value (P10), which was less negative in the abnormal time series. This results from a relative clustering of low RR values more near the median.

Figure 1A:
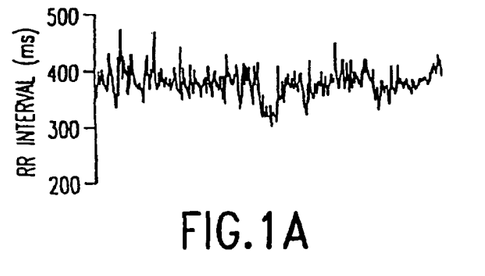
FIGS. 1A-D illustrate four 4096 beat RR interval time series and their frequency histograms.
Figure 1B:
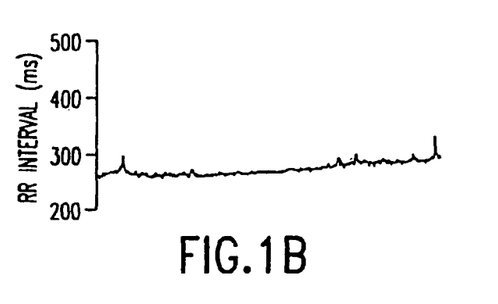
Figure 1C:
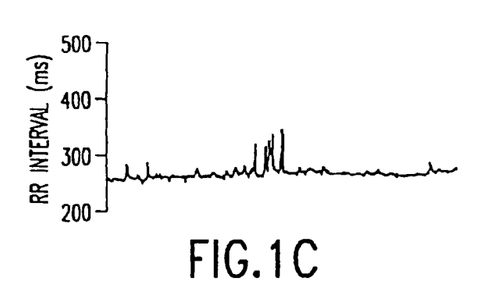
Figure 1D:
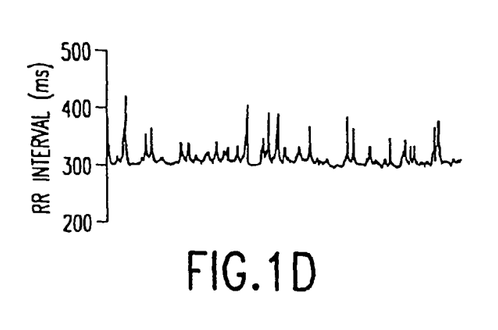
Figure 1E:
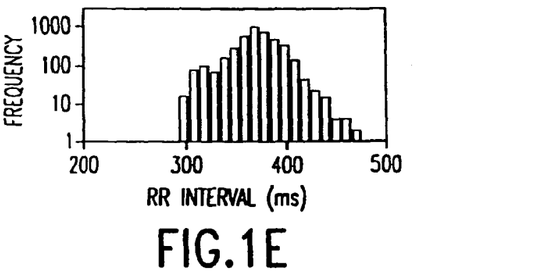
Figure 1F:
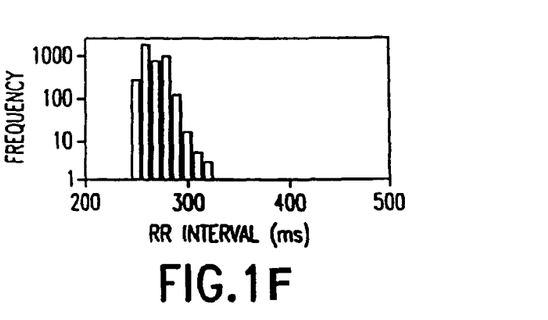
Figure 1G:
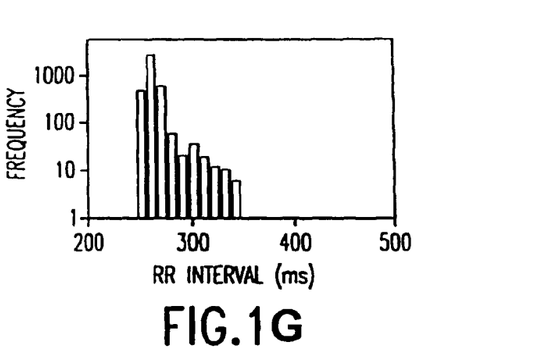
Figure 1H:
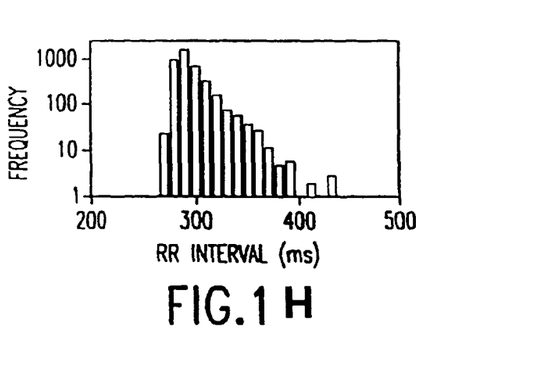
Figure 2A:
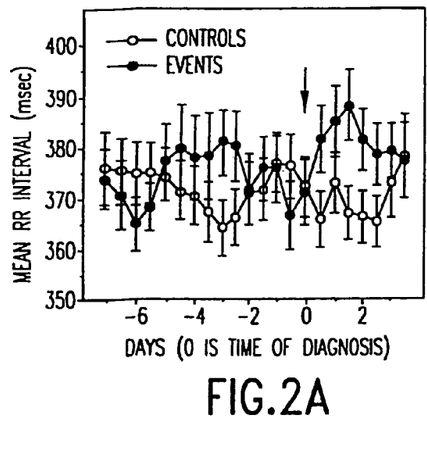
FIGS. 2A-D illustrate the time course of conventional measures of HRV in an events group and a control group. The time labeled 0 is the time that the blood culture was obtained (events group) or was randomly assigned (control group).
Figure 2B:
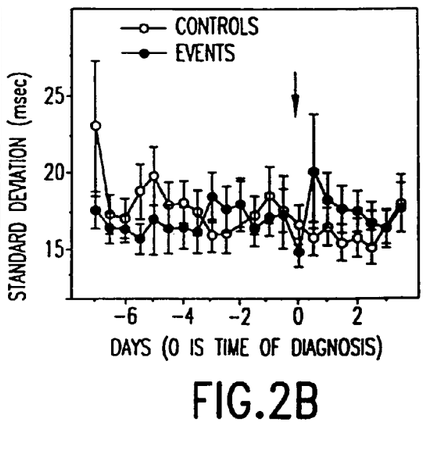
Figure 2C:
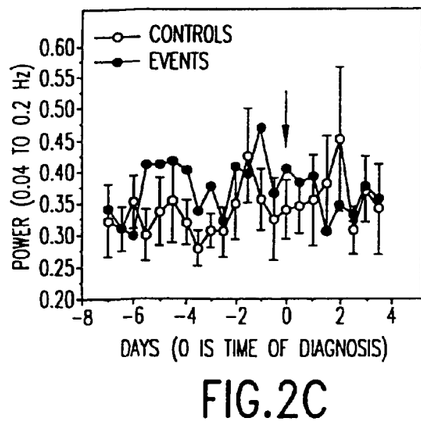
Figure 2D:
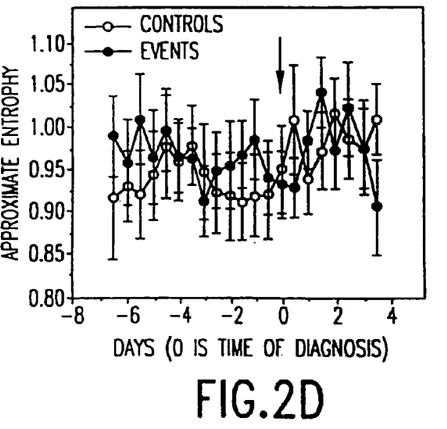
Figure 3A:
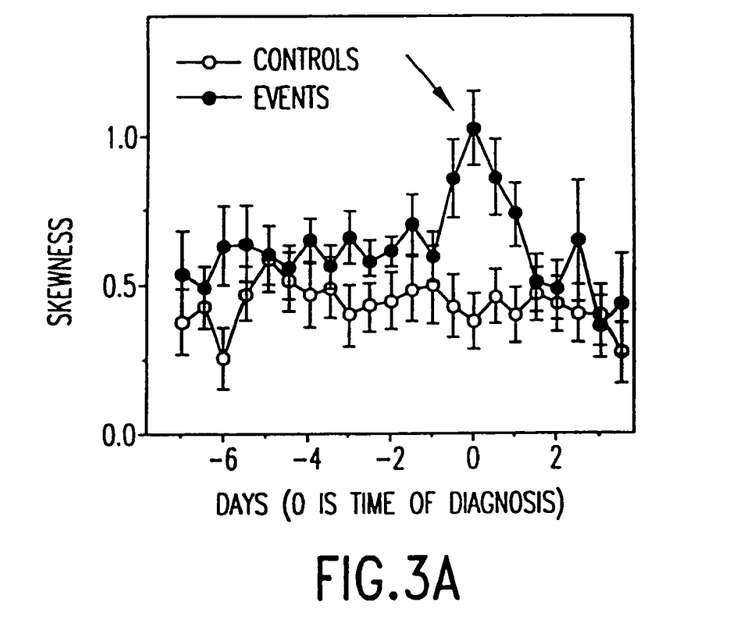
FIGS. 3A and 3B illustrate the time course of skewness and P10 for the events group and control group of FIGS. 2A-D.
Figure 3B:
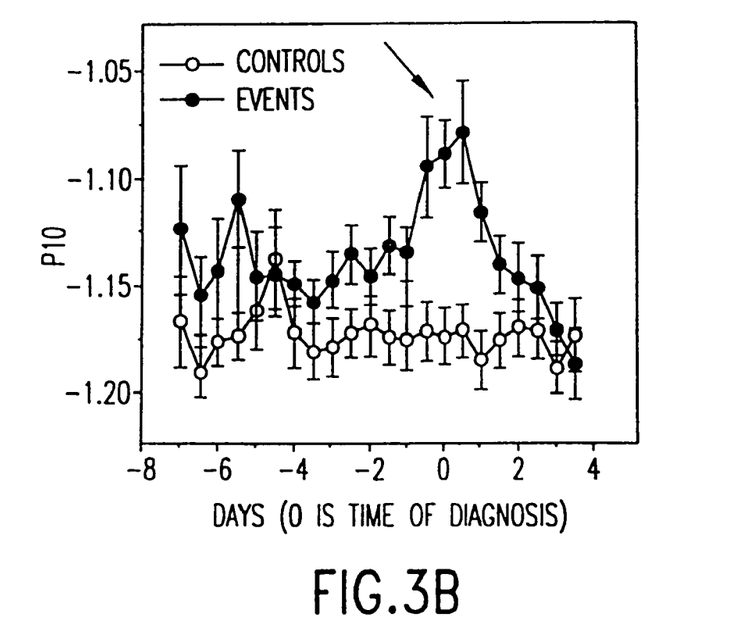

FIGS. 2 and 3 show the time course of HRV measures for the two patient groups. The time labeled 0 is the time that the blood culture was obtained (events group) or was randomly assigned (control group). Each data point is the mean of the median values for a 12 hour epoch ending at the time value on the abscissa. Bars are S.E.M. (standard error of the mean). On the abscissa, 0 marks the index time. Values of mean RR interval (FIG. 2A), standard deviation (FIG. 2B), power from 0.04 to 0.2 Hz (FIG. 2C) and approximate entropy (FIG. 2D) showed no ability to discriminate between the two groups. Similar results were found for power from 0 to 0.04, 0.02 to 0.2, and 0.2 to 1.0 Hz (not shown). The skewness (FIG. 3A) and P10 (FIG. 3B), on the other hand, were markedly different in the two groups in the epochs from 24 hours before to 24 hours after diagnosis. For each of these epochs, the difference between the groups was highly significant (p<0.01, Mann-Whitney rank sum test). Small differences in HRV measures at baseline were noted, despite the differences in gestational and post-conceptional ages.

Example 2

Figure 4:
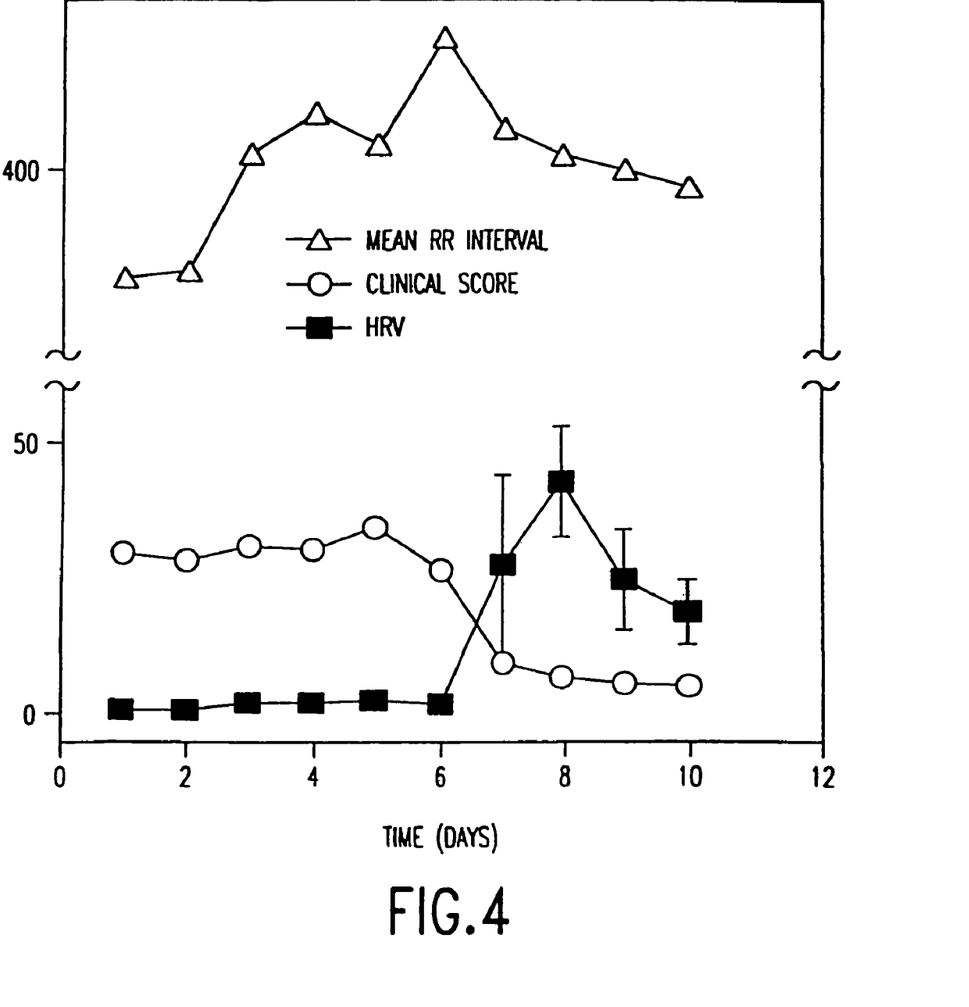
FIG. 4 illustrates time course of the mean RR interval, heart rate variability and clinical score for a clinically ill neonate.

Both HRV and clinical illness severity in 45 NICU infants who were clinically stable was measured. Clinical illness severity was determined using the previously validated Score for Acute Neonatal Physiology (SNAP and SNAP-PE). Richardson, D. K., J. E. Gray, M. C. McCormick, K. Workman, and D. A. Goldmann. 1993. "Score for Neonatal Acute Physiology: a physiologic severity index for neonatal intensive care." *Pediatrics* 91:617-623. Richardson, D. K., C. S. Phibbs, J. E. Gray, M. C. McCormick, K. Workman-Daniels, and D. A. Goldmann. 1993. "Birth weight and illness severity: independent predictors of neonatal mortality." *Pediatrics* 91:969-975. Neonatal Therapeutic Intervention Scoring System (NTISS) was also used. Gray, J. E., D. K. Richardson, M. C. McCormick, K. Workman-Daniels, and D. A. Goldmann. 1992. "Neonatal therapeutic intervention scoring system: a therapy-based severity of illness index." *Pediatrics* 90:561-567. The first assigns points for hemodynamic and laboratory abnormalities; the second for the kinds of therapeutic interventions in use. The higher the clinical score, the more ill the infant may be presumed to be. It was found that the sicker infants, as identified by high clinical scores, had lower HRV. The time course of one of these infants is shown in FIG. 4. The gray triangles are mean RR interval (msec); the open circles are total clinical score; and the black boxes are HRV (measured as power from 0.02 to 0.2 equivalent Hz; msec$^2$). Error bars are S.D. (standard deviation) and are omitted if smaller than the symbol. This figure demonstrates that a decrease in clinical score (i.e. the healthier the infant) correlates to an increase in HRV, while RR interval is less related.

Example 3

Figure 5A:
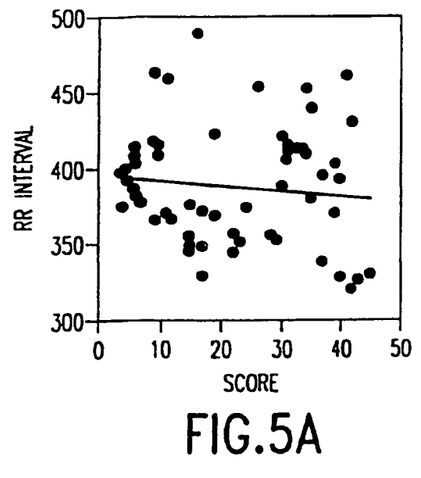
FIG. 5A is a plot of mean heart rate as a function of clinical score for a large group of neonates.
Figure 5B:
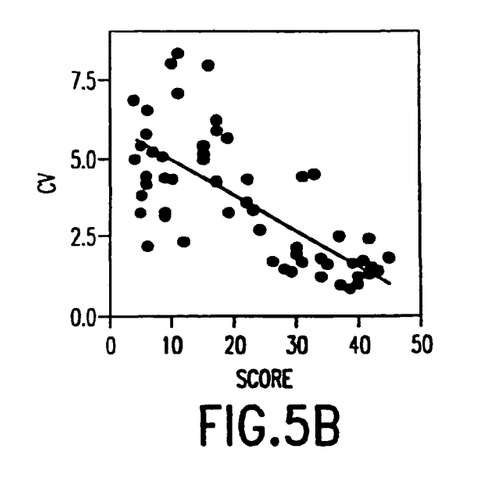
FIG. 5B is a plot of HRV, represented by coefficient of variation ("CV")(standard deviation divided by the mean), as a function of clinical score for a large group of neonates.
Figure 5C:
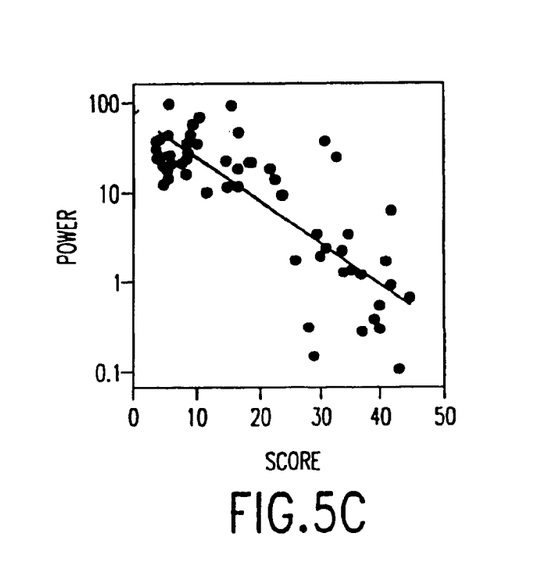
FIG. 5C is a plot of HRV, represented by the power from 0.02 to 0.2 Hz of a moving window of 2048 beats, as a function of clinical score for a large group of neonates.

To test the correlation of HRV and clinical score in a large group of patients, heart rate and HRV, measured in two ways (the coefficient of variation, a time-domain measure and the power from 0.02 to 0.2 equivalent Hz, a frequency domain measure) and were plotted as a function of the clinical score. It was found that there was an inverse correlation for HRV and illness severity: HRV is lower in the sicker infants (those with higher clinical scores.) FIG. 5, panels A, B, and C support this finding. Panel A is a plot of mean heart rate as a function of clinical score. This figure demonstrates that there is no significant correlation between heart rate and clinical score ($r=-0.14$, $p=0.31$). These results were somewhat surprising, as many clinicians would have expected heart rate to rise in the sicker infants. Panels B and C show plots of HRV, represented by coefficient of variation ("CV")(standard deviation divided by the mean) and by the power from 0.02 to 0.2 Hz of a moving window of 2048 beats (panel C). Strong inverse correlations are present ($r>0.7$ and $p<<10^{-2}$ for both). The data in FIGS. 5A, 5B, and 5C represent 81 measurements in 45 infants. HRV was measured over a 3 hour period.

We claim:

1. A method for early detection of subacute, potentially catastrophic illness in an infant comprising:
    (a) monitoring the infant's RR intervals;
    (b) generating a normalized data set of the RR intervals;
    (c) calculating at least one of (i) moments of the data set selected from the third and higher moments, and (ii) percentile values of the data set; and
    (d) identifying an abnormal heart rate variability associated with the illness based on one or more of the moments and percentile values.

2. The method of claim 1, wherein the moments include the third moment of the data set.

3. The method of claim 1, wherein the moments include the fourth moment of the data set.

4. The method of claim 1, wherein the percentile values include the $10^{th}$ data percentile value.

5. The method of claim 1, wherein the infant is a neonate.

6. An apparatus for early detection of subacute, potentially catastrophic infectious illness in a patient, wherein the patient is selected from the group consisting of a premature newborn infant, infant, newborn infant, toddler and child, comprising (1) a monitoring device, continuously monitoring the patient's RR intervals, and (2) a microprocessor, said microprocessor performing steps comprising:
    (a) generating a normalized data set of the RR intervals;
    (b) calculating at least one of (i) moments of the data set selected from the third and higher moments, and (ii) percentile values of the data set; and
    (c) identifying an abnormal heart rate variability based on one or more of the moments and the percentile values.

7. The apparatus of claim 6, wherein the microprocessor calculates the third moment of the data set.

8. The apparatus of claim 6, wherein the microprocessor calculates the fourth moment of the data set.

9. The apparatus of claim 6, wherein the microprocessor calculates the $10^{th}$ percentile of the data set.

* * * * *